United States Patent [19]

Wagner

[11] 4,221,876

[45] Sep. 9, 1980

[54] ISOCYANATE-REACTIVE MIXTURES BASED ON FORMOSE

[75] Inventor: Kuno Wagner, Leverkusen, Fed. Rep. of Germany

[73] Assignee: Bayer Aktiengesellschaft, Leverkusen, Fed. Rep. of Germany

[21] Appl. No.: 934,566

[22] Filed: Aug. 17, 1978

[30] Foreign Application Priority Data

Aug. 26, 1977 [DE] Fed. Rep. of Germany ....... 2738533
May 11, 1977 [DE] Fed. Rep. of Germany ....... 2721186

[51] Int. Cl.² .............................................. C08G 18/14
[52] U.S. Cl. ...................................... 521/158; 127/30;
127/31; 252/182; 568/376; 568/388; 568/414;
568/461; 528/85; 568/496; 568/497; 536/1
[58] Field of Search ......................... 521/158; 252/182;
260/594, 602; 536/1; 127/30, 31; 528/85

[56] References Cited

U.S. PATENT DOCUMENTS

| | | | |
|---|---|---|---|
| 2,269,935 | 1/1942 | Hanford et al. | 260/594 |
| 2,760,983 | 8/1956 | McLean | 260/594 |
| 3,202,620 | 8/1965 | Merten et al. | 521/158 |

*Primary Examiner*—Maurice J. Welsh
*Attorney, Agent, or Firm*—Gene Harsh; Joseph C. Gil; Bruce E. Harang

[57] ABSTRACT

This invention relates to mixtures, in the form of relatively low viscosity liquids at room temperature, of formose, aldehydes and/or ketones aldolated in the α-position and, optionally, water and/or crystalline mono- or di-saccharides, and to the use of these mixtures for the production of polyurethane plastics, particularly foams.

31 Claims, No Drawings

ISOCYANATE-REACTIVE MIXTURES BASED ON FORMOSE

This application is a continuation-in-part application of Ser. No. 829,173 filed Aug. 30, 1977.

BACKGROUND OF THE INVENTION

In the context of the invention, the expression "formose" applies to the mixtures known per se of low molecular weight polyhydroxyl compounds (polyhydric alcohols, hydroxy aldehydes and hydroxy ketones) which are formed by the condensation of formaldehyde hydrate.

The production of mixtures of polyhydric alcohols, hydroxy aldehydes and hydroxy ketones by the autocondensation of formaldehyde hydrate is described in numerous literature references. (See e.g. Butlerow and Loew, Annalen 120, 295 (1861) and J. pr. Chem. 33, 321 (1886); Pfeil, chemische Berichte 84, 229 (1951); Pfeil and Schroth, chemische Berichte 85, 303 (1952); R. D. Partridge and A. H. Weiss, Carbohydrate Research 24, 29–44 (1972); the formoses of glycerol aldehyde and dioxy acetone according to Emil Fischer; German Pat. Nos. 882,385; 830,951 and 884,794; U.S. Pat. Nos. 2,224,910; 2,269,935 and 2,272,378 and British Pat. No. 513,708.) However, these conventional processes have certain disadvantages such as toxic catalyst, poor volume-time yields and discoloring secondary products. New processes have recently been developed by which it is possible to produce substantially colorless formoses free from troublesome secondary products in high yields using conventional catalysts.

One of these new processes comprises condensing formaldehyde hydrate in the presence of soluble or insoluble lead(II)salts or lead(II)ions fixed to high molecular weight supports as catalysts and in the presence, as co-catalyst, of a mixture of hydroxy aldehydes and hydroxy ketones such as is formed in the condensation of formaldehyde hydrate and which has the following molar ratios:

Compounds containing 3 carbon atoms/compounds containing 4 carbon atoms: 0.5:1 to 2.0:1
Compounds containing 4 carbon atoms/compounds containing 5 carbon atoms: 0.2:1 to 2.0:1
Compounds containing 5 carbon atoms/compounds containing 6 carbon atoms: 0.5:1 to 5.0:1.

The proportion of components containing from 3 to 6 carbon atoms should be at least 75% by weight and preferably to more than 85% by weight, based on the total co-catalyst.

The reaction temperature is generally held in the range from 70° to 110° C. and preferably in the range from 80° to 100° C. The pH-value of the reaction solution is adjusted by the controlled addition of an inorganic or organic base up to a conversion of from 10 to 60%, preferably from 30 to 50%, to a value of from 6.0 to 8.0 and preferably to a value of from 6.5 to 7.0, and then to a value of from 4.0 to 6.0 and preferably to a value of from 5.0 to 6.0. It has surprisingly been found that the product distribution of the corresponding polyol, hydroxy aldehyde and hydroxy ketone mixtures can be varied reproducibly by this special pH-profile and by subsequent cooling at different residual formaldehyde contents (0 to 10% by weight, preferably 0.5 to 6% by weight).

After the autocondensation of the formaldehyde hydrate has been interrupted by cooling and/or by deactivating the lead-containing catalyst with acids, the catalyst may be removed in known manner and the water present in the products is evaporated. For further particulars, see German Offenlegungsschrift No. 2,639,084.

Another possible method for obtaining highly concentrated colorless formoses in high volume-time yields is to condense aqueous formalin solutions and/or paraformaldehyde dispersions in the presence of a soluble or insoluble metal catalyst and a co-catalyst produced by partial oxidation of a dihydric or polyhydric alcohol containing at least two vicinal hydroxyl groups and having a molecular weight of from 62 to 242 or a mixture of such alcohols. The pH-value of the reaction solution is being kept between 6.0 and 9.0 by the controlled addition of a base up to a conversion of from 5 to 40% and is subsequently adjusted to between 4.5 and 8.0 to terminate the condensation reaction so that the pH-value is then 1.0 to 2.0 units lower than in the first phase of the reaction. The reaction is then interrupted by deactivating the catalyst at a residual formaldehyde content of from 0 to 10% by weight and the catalyst removed. This process is described in detail in German Offenlegungsschrift No. 2,714,084.

High-quality formoses can also be obtained by condensing formaldehyde in the presence of a metal catalyst and more than 10% by weight, based on formaldehyde, of one or more dihydric or polyhydric low molecular weight alcohols and/or relatively high molecular weight polyhydroxyl compounds. Formose-polyol mixtures such as these are the subject of German Offenlegungsschrift No. 2,714,104.

The properties of the formose (i.e. the average hydroxyl functionality, degree of branching and content of reducing groups) may be widely varied, depending upon the manner in which condensation of the formaldehyde is carried out. In general, the average molecular weight and, hence, the hydroxyl functionality of the formoses, increases as the condensation reaction is continued, i.e. as the quantity of residual formaldehyde present when the condensation reaction is terminated is lowered. Thus, if the condensation reaction is continued up to a residual formaldehyde content of from 0 to 1.5% by weight, the formose obtained contains approximately 25% by weight of compounds containing 5 carbon atoms, 45% by weight of compounds containing 6 carbon atoms and approximately 20% by weight of compounds containing 7 or more carbon atoms. By contrast, a total of only about 10% of polyols, hydroxy ketones and hydroxy aldehydes containing 2, 3, and 4 carbon atoms is obtained. This corresponds to an average hydroxyl functionality of approximately 5.

As explained above, other component distributions of the starter mixtures are obtained by terminating autocondensation of the formaldehyde at somewhat higher residual formaldehyde contents. Thus, termination of the condensation reaction at a formaldehyde content of from 2 to 2.5% gives a mixture of polyhydric alcohols, hydroxy aldehydes and hydroxy ketones having an average hydroxyl functionality of approximately 4. Other component distributions having an even more reduced average hydroxyl functionality are obtained by terminating the condensation reaction at residual formaldehyde contents of greater than 2.5.

By mixing the formose with difunctional or more highly functional low molecular weight alcohols, the functionality of the products may be further varied in cases where it is desired to obtain certain specified properties. Suitable low molecular weight polyhydric alcohols of this type having molecular weights of up to about 300 include ethylene glycol, 1,2-propane diol, 1,3-propane diol, 1,4-butane diol, diethylene glycol, dipropylene glycol, triethylene glycol, tetraethylene glycol, dibutylene glycol, glycerol, trimethylol propane, pentaerythritol, sorbitol, butane triols and hexane triols and the like as well as ethoxylation products of these alcohols or even hydrogenated formose (formitol).

It is also possible to use amines and/or ethanolamines as a mixing component. Examples include mono-, di- and tri-ethanolamine, mono-, di- and tri-isopropanolamine, N-alkanolamines, such as N-methyl diethanolamine and N-ethyl diethanolamine, and lower aliphatic monoamines and polyamines, such as ethylamine, ethylene diamine, diethylene triamine and triethylene tetraamine.

According to earlier proposals in particular the already mentioned e.g. German Offenlegungsschriften Nos. 2,639,084; 2,714,084 and 2,714,104, formoses may be used as polyol components in the polyisocyanate polyaddition process for the production of polyurethane plastics.

DESCRIPTION OF THE INVENTION

It has now been found that polyurethane plastics, particularly foams, showing improved flameproof properties can be obtained by using a mixture of formose and α-methylolated aldehydes and/or ketones instead of pure formose as the starting component. Compared with pure formose, such mixtures generally show a reduced viscosity which is of considerably practical advantage because the mixtures can be readily metered with conventional equipment. In addition, the mixtures of formose and α-methylolated aldehydes or ketones surprisingly have the ability of being able to dissolve large quantities of crystallized sugars (monosaccharides and/or disaccharides). They are also miscible within wide limits with waterglass.

Accordingly, the present invention relates to isocyanate-reactive mixtures comprising (a) 20 to 90% by weight, preferably 40 to 70% by weight, based on (a)+(b), of a mixture of polyhydric alcohols, hydroxy aldehydes and hydroxy ketones which have been obtained by the condensation of formaldehyde hydrate, (b) 10 to 80% by weight, preferably 25 to 60% by weight, based on (a)+(b), of aldehydes and/or ketones methylolated in the α-position and incapable of endiol formation, (c) 0 to 50% by weight, preferably 0.3 to 30% by weight and, with particular preference, 0.8 to 10% by weight, based on (a)+(b) of water and (d) 0 to 100% by weight, preferably 10 to 50% by weight, based on (a)+(b), of monosaccharides and/or disaccharides.

In principle, any formoses may be used for the mixtures according to the invention. For the preferred application, which is the production of polyurethane plastics, however, it is of advantage to use the formoses produced by the above-described processes because they are generally colorless and free from troublesome secondary products. It is preferred to use formoses which have an average molecular weight of from 92 to 360, more preferably from 100 to 240 and a sugar content (expressed as glucose having a molecular weight of 180) of from 4 to 85% by weight, and more preferably, from 6 to 72% by weight. In addition, formoses which have been α-aldolated by subsequent treatment with formaldehyde in basic pH-ranges are preferred for some applications because of their relatively high content of primary hydroxyl groups. According to the invention, it is of course also possible to use formoses which contain formaldehyde still bound in the form of semiacetals or which have been intermolecularly or intramolecularly acetalated or ketalated by subsequent treatment with acids. In the context of the present invention, all of these products are covered by the expression "formose".

Aldehydes and ketones methylolated in the α-position which do not contain any hydroxyl group in the α-position (in contrast to the carbonyl compounds of formose) and which are therefore incapable of endiol formation, may be used as component (b) in the mixtures according to the invention. These aldehydes and ketones may be aliphatic, cycloaliphatic or araliphatic. They preferably contain from 2 to 15 carbon atoms, and more preferably, from 2 to 9 carbon atoms including the carbonyl group.

Examples of suitable aldehydes and ketones include acetaldehyde, acetone, propionaldehyde, butyraldehyde, isobutyraldehyde, methylethyl ketone, cyclopentanone, cyclohexanone, mesityl oxide, isophorone, acetophenone and their methylol derivatives which may be obtained by base-catalyzed partial or complete aldolation with formaldehyde on the carbon-atoms in the α-position to the carbonyl group. Examples of these derivatives are compounds corresponding to the following formulae:

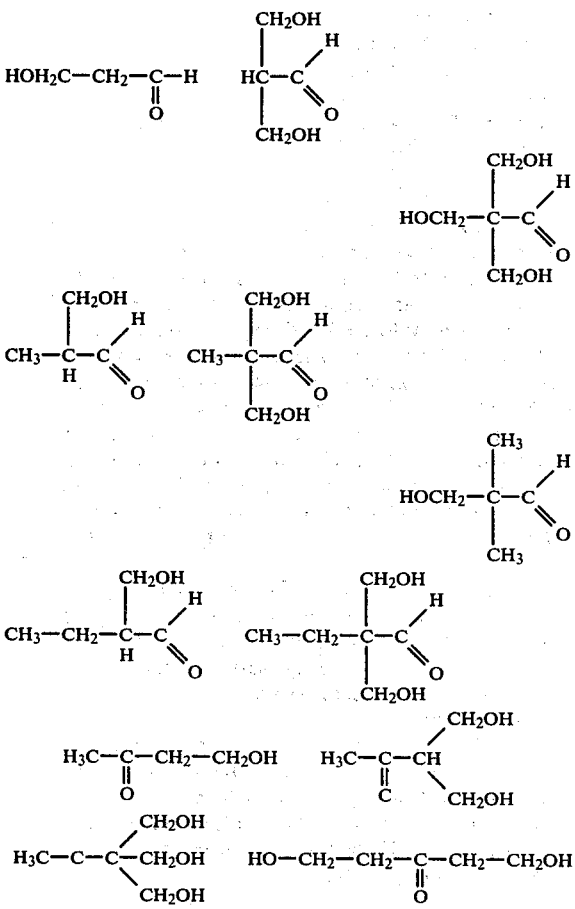

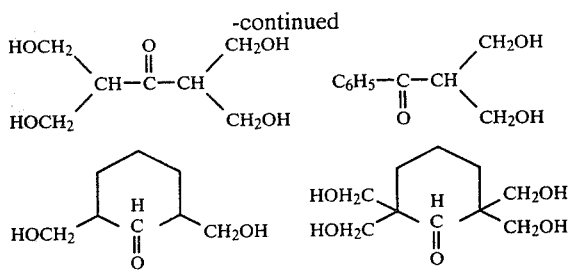

According to the invention, it is particularly preferred to use n-butryaldehyde, isobutyraldehyde, acetone and cyclohexanone or their methylolation products.

As already mentioned, relatively large quantities of crystallized monosaccharides and disaccharides such as glucose, maltose or cane sugar, are surprisingly soluble in the mixtures according to the invention. Also soluble are natural invert sugars such as bee's honey; artificial invert sugars such as hydrolysates of cane sugar; hydrolysates of corn starch, potato starch, of pectins, or hydrolysates of any other disaccharides and/or polysaccharides, such as trehalose, galactose, raffinose, cellulose and dextrins. This is of particular commercial interest because crystallized monosaccharides and disaccharides such as these are difficult to react with polyisocyanates in pure form.

The mixtures according to the invention are preferably obtained by carrying out the condensation of formaldehyde in the presence of the above-mentioned α-aldolatable aldehydes or ketones or their methylolation products in accordance with the processes described above. Although, as already mentioned, the α-aldolatable carbonyl compounds to be added in accordance with the invention are not capable of endiol formation, it has surprisingly been found that they perform a co-catalytic function in the autocondensation of formaldehyde hydrate, with the result that there is no need to add the usual cocatalysts based on compounds capable of endiol formation.

Accordingly, the present invention also relates to a process for producing the mixtures according to the invention, wherein aqueous formalin solutions and/or paraformaldehyde dispersions containing from 20 to 65% by weight of formaldehyde are condensed at pH-values of from 4 to 9 and preferably at pH-values of from 5 to 8 and at a reaction temperature of from 70° to 110° C. in the presence of (a) soluble or insoluble salts of metals of the Second to Fourth Main Group or of the First to Eighth Secondary Group of the Periodic System of Elements or metal ions fixed to a high molecular weight support,
(b) aldehydes and/or ketones capable of α-aldolation or their α-methylolation products and, optionally,
(c) co-catalysts based on compounds capable of endiol formation, until the residual formaldehyde content is from 0 to 10% by weight, preferably from 0.5 to 6% by weight, based on the reaction mixture. The catalyst is subsequently removed in known manner and the reaction product concentrated to the required water content.

As already mentioned, the above-mentioned α-aldolatable carbonyl compounds may be added in raw form because they are methylolated very rapidly under the above-mentioned reaction conditions. According to the invention, however, it is of course also possible to add the α-methylolated carbonyl compounds to the reaction mixture from the outset. However, it is preferred to couple synthesis of the formose with the methylolation of the aldehydes or ketones. In this case, it is particularly advisable, for controlling the pH-value, to use organic bases, preferably tertiary amines, and particularly sterically hindered soluble amines such as diisobutylamine, triisobutylamine, diisopropylamine, N,N-dimethyl cyclohexylamine or N-methyl isopropyl cyclohexylamine. In this case, the α-methylolation reaction is largely unaccompanied by troublesome Cannizzaro or crossed Cannizzaro reactions. The methylolation of the aldolatable aldehydes and ketones to be added in accordance with the invention takes place much more quickly than α-methylolation reactions of the formose because most of the aldehyde and keto groups of the formose are blocked by cyclosemiacetal or ketal formation.

Secondary products from the commercial production of trimethylol propane from butyraldehyde and formaldehyde such as, for example, 2-ethylacrolein may also be used for condensation of the formaldehyde into formose. In this case, 2-ethylacrolein, for example, is converted into 2,2-dimethylol alkanal in the presence of tertiary amine catalysts, such as triisobutylamine:

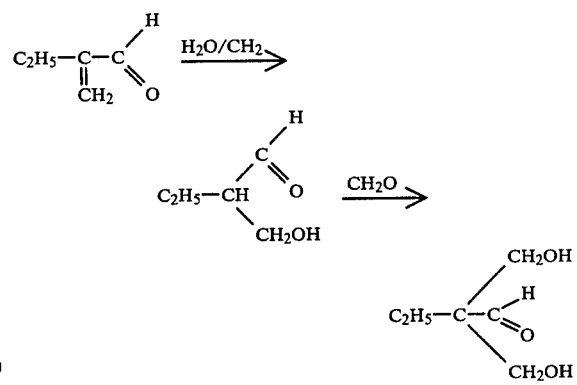

These methylolated aldehydes and ketones also lead to an advantageous reduction in the viscosity of the formoses produced in accordance with the invention.

The mixtures of formose and α-methylolated carbonyl compounds according to the invention may also be produced by continuing the reaction by which the formaldehyde is condensed into formose up to a conversion of only from 40 to 95%, preferably from 70 to 90%, based on the formaldehyde used, and then removing the residual formaldehyde by the addition of α-methylolatable carbonyl compounds incapable of endiol formation, preferably after deactivation of the formose catalyst, In this case, it is preferred to work in a pH-range from 7 to 9 in the presence of the usual inorganic bases. Alternatively, if Cannizzaro reactions are to be avoided, it is best to carry out the reaction in the presence of the above-mentioned organic bases.

The present invention also relates to a process for producing the mixtures according to the invention of formose and α-methylolated carbonyl compounds incapable of endiol formation, wherein aqueous formalin solutions and/or paraformaldehyde dispersions containing from 20 to 65% by weight of formaldehyde are condensed at pH-values of from 4 to 9, preferably from 5 to 8, at a reaction temperature of from 70° to 110° C. in the presence of (a) soluble or insoluble salts of metals of the Second to Fourth Main Group or of the First to Eighth Secondary Group of the Periodic System of Elements or metal ions fixed to a high molecular weight support, and
(b) a co-catalyst based on compounds capable of enediol formation, up to a conversion of from 40 to 95%, preferably from 70 to 90%, based on the formaldehyde used, to form mixtures of low molecular weight polyhydric alcohols, hydroxy aldehydes and hydroxy ketones. The residual formaldehyde is bound by the addition of α-aldolatable carbonyl compounds incapable of enediol formation and the reaction product is subsequently freed from the catalyst in known manner and concentrated to the required water content.

With regard to the catalysts and co-catalysts to be used in the two above-mentioned variations of the process for producing the mixtures according to the invention, reference is made to the disclosures of German Offenlegungsschriften Nos. 2,639,084, 2,714,084 and 2,714,104, which are herein incorporated by reference.

It is of course also possible to produce the mixtures according to the invention by introducing the α-aldolatable carbonyl compounds into a formaldehyde-free aqueous or alcoholic formose solution produced by any method, or vice versa, subsequently adding aqueous formaldehyde in the quantity necessary for the required degree of methylolation, methylolating the carbonyl compounds and subsequently removing the excess water, for example in a thin-film evaporator under a vacuum of from 1 to 18 Torr and at a temperature of from 35° to 60° C. In general, from about 20 to 300% and preferably from 50 to 150% of the quantity of formaldehyde required to obtain complete methylolation of the α-aldolatable carbonyl compounds is added in this variant of the process. This subsequent methylolation reaction is also preferably carried out at pH-values in the range from 7 to 9 and, with particular preference, at pH-values in the range from 7.5 to 8, and at temperatures of from 10° to 65° C. and, with particular preference, at temperatures of from 20° to 50° C. in the presence of the above-mentioned organic bases.

The present invention also relates to a process for producing the mixtures according to the invention of formose and α-methylolated carbonyl compounds incapable of enediol formation, wherein an aqueous or alcoholic solution of a mixture of low molecular weight polyhydric alcohols, hydroxy aldehydes and hydroxy ketones which has been obtained by the autocondensation of formaldehyde hydrate is mixed with α-aldolatable carbonyl compounds, and subsequently methylolated by the addition of aqueous formaldehyde. Optionally, the excess water is subsequently removed in known manner.

If more than the quantity of formaldehyde required to obtain complete methylolation of the aldolatable carbonyl compounds added is used for this subsequent modification of formose, methylolation reactions also occur to an increasing extent on the α-carbon atoms of carbonyl groups of the formose.

This α-methylolation increases the functionality and reactivity of the end products with respect to isocyanates because additional primary hydroxyl groups are introduced into the formose. These aldolation reactions take place by way of the open-chain forms of the sugars which exist in equilibrium with the cyclo-semiacetals of the sugars.

According to the invention, it is possible to accelerate the α-methylolation reactions in the form of a heterogeneous catalysis by the addition of moderately to strongly basic ion exchangers. In this way the caramelization reactions of the sugars which normally occur at relatively high pH-values are significantly suppressed and the acids formed during synthesis of the formose are partly bound.

The processes for producing the mixtures according to the invention may of course also be carried out continuously in a reaction tube. In order to adjust the required pH-value in the reaction volume, the inorganic or organic base is continuously added in the requisite quantity at one or more points of the tube. In this case, it is also possible to vary the product distribution and hydroxyl functionality of the resulting mixtures over a wide range by varying the throughflow times.

It is of course also possible, although less preferred, to produce the mixtures according to the invention simply by mixing formaldehyde-free-aqueous formose solutions produced by any method with the methylolated aldehydes or ketones.

The crystalline sugars also are similarly introduced into the mixtures by adding the sugars at any stage during or after the production of the formose modified in accordance with the invention.

Up to 150% by weight, preferably from 10 to 100% by weight, of fillers, such as for example aluminum oxide hydrate, may be stirred into the mixtures according to the invention. Stable, non-sedimenting paste-like dispersions are formed. These dispersions are particularly suitable for the production of filler-containing polyurethane foams.

As already mentioned, the principle intended application for the products of the present process is in the production of flame-resistant polyurethane plastics, and particularly polyurethane foams.

Accordingly, the present invention also relates to a process for the production of optionally cellular polyurethane plastics by reacting
(A) polyisocyanates with
(B) polyhydroxyl compounds having a molecular weight of less than 400, optionally
(C) polyhydroxyl compounds having a molecular weight of from 400 to 10,000 and, optionally, other isocyanate-reactive compounds, optionally in the presence of
(D) blowing agents, catalysts, fillers and other additives known per se, wherein the mixtures according to the invention described above, are used as component (B).

Since the mixtures according to the invention generally contain relatively large quantities of water, and since the water can only be completely removed from formose mixtures with considerable capital outlay, the mixtures according to the invention are particularly suitable for the production of polyurethane foams. Depending upon the recipe used, it is possible according to the invention to produce both open-cell and closed-cell rigid polyurethane foams as well as open-cell flexible foams.

For producing open-cell rigid foams, it is best to use mixtures according to the invention which contain from 4 to 25% by weight, preferably from 8 to 20% by weight of water. The above-described suspensions of aluminum oxide hydrate or other mineral fillers may also be used in the mixtures of the invention. It is also possible, if desired to use up to 100% by weight, preferably from 10 to 50% by weight, based on the total polyol component, of a relatively high molecular weight polyhydroxyl compound having a molecular weight from about 400 to 10,000 as an elasticizing component. The quantity of the polyisocyanate in the recipe may vary within wide limits. It is possible to use either an excess up to 120% of the calculated equivalent quantity, a less than equivalent quantity of polyisocyanate, based on the sum total of isocyanate-reactive components present. However, it has been found that the lower the index of the recipe, the better are the flame-resistant properties of the foams (the index is the equivalent ratio of polyisocyanates to isocyanate-reactive compounds). Accordingly, the recipes used preferably have indices in the range from 20 to 70 more preferably 30 to 60, and most preferably in the range from 35 to 55.

For producing closed-cell rigid foams, it is preferred to use mixtures according to the invention which contain from 0 to 4% by weight, more preferably 0.7 to 3% by weight, of water. In this case, foaming is obtained by the addition of low-boiling liquids, such as fluorotrichloromethane, for example. So far as the index of the recipes is concerned, the comments made above with reference to the open-cell rigid foams also apply in this case.

The mixtures according to the invention may also be used in quantities of from 5 to 30% by weight and preferably in quantities of from 5 to 20% by weight, based on the total polyol component, as cross-linking agent in the production of open-cell flexible foams. In this case, the rest of the polyol component consists of polyhydroxyl compounds having a molecular weight of from 400 to 10,000, preferably of polyether polyols.

Suitable isocyanate components for the production of the polyurethane plastics are known and include the aliphatic, cycloaliphatic, araliphatic, aromatic and heterocyclic polyisocyanates described for example, by W. Siefken in Justus Liebigs Annalen der Chemie, 562, pages 75 to 136. Suitable examples include ethylene diisocyanate; 1,4-tetramethylene diisocyanate; 1,6-hexamethylene diisocyanate; 1,12-dodecane diisocyanate; cyclobutane-1,3-diisocyanate; cyclohexane-1,3- and 1,4-diisocyanate, and mixtures of these isomers; 1-isocyanato-3,3,5-trimethyl-5-isocyanatomethyl cyclohexane as described in German Auslegeschrift No. 1,202,785 and U.S. Pat. No. 3,401,190; 2,4- and 2,6-hexahydrotolylene diisocyanate, and mixtures of these isomers; hexahydro-1,3- and/or 1,4-phenylene diisocyanate; perhydro-2,4' and/or -4,4'-diphenyl methane diisocyanate; 1,3- and 1,4-phenylene diisocyanate; 2,4- and 2,6-tolylene diisocyanate, and mixtures of these isomers; diphenyl methane-2,4'- and/or -4,4'-diisocyanate; naphthylene-1,5-diisocyanate; triphenyl methane-4,4',4''-triisocyanate; polyphenyl polymethylene polyisocyanates, of the type which can be obtained by condensing aniline with formaldehyde, followed by phosgenation, and which are described, for example, in British Pat. Nos. 874,430 and 848,671; m- and p-isocyanatophenyl sulphonyl isocyanates as described in U.S. Pat. No. 3,454,606; perchlorinated aryl polyisocyanates of the type described, for example, in German Auslegeschrift No. 1,157,601 and U.S. Pat. No. 3,277,138; polyisocyanates containing carbodiimide groups of the type described in German Pat. No. 1,092,007 and U.S. Pat. No. 3,152,162; diisocyanates of the type described in U.S. Pat. No. 3,492,330; polyisocyanates containing allophanate groups of the type described, for example in British Pat. No. 994,890, Belgian Pat. No. 761,626 and published Dutch patent application No. 7,102,524; polyisocyanates containing isocyanurate groups of the type described, for example, in U.S. Pat. No. 3,001,973, German Pat. Nos. 1,022,789, 1,222,067 and 1,027,394 and in German Offenlegungsschrifts Nos. 1,929,034 and 2,004,048; polyisocyanates containing urethane groups of the type described, for example, Belgian Pat. No. 752,261 or in U.S. Pat. No. 3,394,164; polyisocyanates containing acylated urea groups as described in German Pat. No. 1,230,778; polyisocyanates containing biuret groups of the type described, for example, in German Pat. No. 1,101,394 and U.S. Pat. Nos. 3,124,605 and 3,201,372 and in British Pat. No. 889,050; polyisocyanates obtained by telomerization reactions of the type described, for example, in U.S. Pat. No. 3,654,106; polyisocyanates containing ester groups of the type described, for example, in British Pat. Nos. 965,474 and 1,072,956, U.S. Pat. No. 3,567,763 and German Pat. No. 1,231,688; reaction products of the above-mentioned isocyanates with acetals as described in German Pat. No. 1,072,385; and polyisocyanates containing polymeric fatty acid radicals as described in U.S. Pat. No. 3,455,883.

It is also possible to use the isocyanate-group-containing distillation residues obtained in the commercial production of isocyanates, optionally in solution in one or more of the aforementioned polyisocyanates. It is also possible to use any mixtures of the aforementioned polyisocyanates.

In general, it is particularly preferred to use readily available polyisocyanates, such as 2,4- and 2,6-tolylene diisocyanate as well as any mixtures of these isomers ("TDI"); polyphenyl polymethylene polyisocyanates of the type obtained by condensing aniline with formaldehyde, followed by phosgenation ("crude MDI"); and polyisocyanates containing carbodiimide groups, urethane groups, allophanate groups, isocyanurate groups, urea groups or biuret groups ("modified polyisocyanates").

Suitable relatively high molecular weight polyhydroxyl compounds, particularly those with molecular weights in the range from 800 to 10,000, and preferably in the range from 1000 to 6000 include polyesters, polyethers, polythioethers, polyacetals, polycarbonates and polyester amides containing at least 2, generally 2 to 8, but preferably 2 to 4 hydroxyl groups, of the type commonly used for the production of homogeneous and cellular polyurethanes.

Examples of suitable polyesters containing hydroxyl groups are reaction products of polyhydric alcohols (preferably dihydric alcohols to which, trihydric alcohols may be added) with polybasic (preferably dibasic) carboxylic acids. Instead of the free polycarboxylic acids, the corresponding polycarboxylic acid anhydrides or corresponding polycarboxylic acid esters of lower alcohols or mixtures thereof may also be used for the production of the polyesters. The polycarboxylic acids may be aliphatic, cycloaliphatic, aromatic and/or heterocyclic, and may be substituted, for example by halogen atoms, and/or they may be unsaturated. Examples of these polycarboxylic acids are succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid, which may be in admixture with monomeric fatty acids, terephthalic acid dimethyl ester, terephthalic acid-bis-glycol ester. Examples of suitable polyhydric alcohols are ethylene glycol, 1,2- and 1,3-propylene glycol, 1,4- and 2,3-butylene glycol, 1,6-hexanediol, 1,8-octanediol, neopentyl glycol, cyclohexane dimethanol (1,4-bis-hydroxy methyl cyclohexane), 2-methyl-1,3-propane diol, glycerol, trimethylol propane, 1,2,6-hexane triol, 1,2,4-butane triol, trimethylol ethane, pentaerythritol, quinitol, mannitol and sorbitol, methyl glycoside, diethylene glycol, triethylene glycol, tetraethylene glycol, polyethylene glycols, dipropylene glycol, polypropylene glycols, dibutylene glycol and polybutylene glycols. The polyesters may contain terminal carboxyl groups. Polyesters of lactones, for example, ε-caprolactone or hydroxy carboxylic acids, for example ω-hydroxy caproic acid, may also be used.

The polyethers containing at least 2, generally 2 to 8 and preferably 2 to 3 hydroxyl groups which may be used in accordance with the invention are also known per se. They are obtained, for example, by the polymerization of epoxides such as ethylene oxide, propylene oxide, butylene oxide, tetrahydrofuran, styrene oxide or epichlorhydrin on their own, for example in the presence of boron trifluoride, or by the chemical addition of these epoxides, either in admixture or in succession, to starter components containing reactive hydrogen atoms such as water, alcohols or amines, for example, ethylene glycol, 1,3- or 1,2-propylene glycol, trimethylol propane, 4,4'-dihydroxy diphenyl propane, aniline, ammonia, ethanolamine, ethylene diamine. In many cases, it is preferred to use polyethers of the kind which contain major amounts primary hydroxyl groups (up to 90% by weight, based on all the hydroxyl groups present in the polyether). Polyethers modified by vinyl polymers of the kind obtained, for example, by the polymerization of styrene, acrylonitrile in the presence of polyethers as described in U.S. Pat. Nos. 3,383,351; 3,304,273; 3,523,093 and 3,110,695 and German Pat. No. 1,152,536 as well as polybutadienes containing hydroxyl groups are also suitable.

Among the polythioethers, reference is made in particular to the condensation products of thiodiglycol with itself and/or with other glycols, dicarboxylic acids, formaldehyde, amino carboxylic acids or amino alcohols. Depending upon the co-components, these products are polythio mixed ethers, polythioether esters, polythioether ester amides.

Suitable polyacetals include, those compounds which can be obtained from glycols, such as diethylene glycol, triethylene glycol, 4,4'-dioxethoxy diphenyl dimethyl methane, hexane diol and formaldehyde. Polyacetals suitable for the purposes of the invention may also be obtained by polymerizing cyclic acetals.

Suitable polycarbonates containing hydroxyl groups are those known per se obtainable, for example, by reacting diols such as 1,3-propane diol, 1,4-butane diol and/or 1,6-hexane diol, diethylene glycol, triethylene glycol, tetraethylene glycol, with diaryl carbonates, for example diphenyl carbonate, or phosgene.

Examples of the polyester amides and polyamides are the predominantly linear condensates obtained from polybasic, saturated and unsaturated carboxylic acids and their anhydrides and polyhydric saturated and unsaturated amino alcohols, diamines, polyamines and their mixtures.

Polyhydroxyl compounds already containing urethane or urea groups and natural polyols, which may be modified, such as castor oil, carbohydrates, starch, may also be used. Addition products of alkylene oxides with phenol-formaldehyde resins or even with urea-formaldehyde resins may also be used in accordance with the invention.

Representatives of the many and varied compounds used in accordance with the invention are described, for example in High Polymers, Vol. XVI, "Polyurethanes, Chemistry and Technology", by Saunders-Frisch, Interscience Publishers, New York, London, Vol. 1, 1962, pages 32 to 42 and pages 44 to 54, and Vol. II, 1964, pages 5–6 and 198–199, and in Kunststoff-Handbuch, Vol. VII, Vieweg-Hochtlen, Carl-Hanser-Verlag, Munich, 1966, for example on pages 45 to 71.

It is of course also possible to use mixtures of the above-mentioned compounds containing at least two isocyanate-reactive hydrogen atoms and having a molecular weight of from 800 to 10,000, for example mixtures of polyethers and polyesters.

Other starting components which may be used in accordance with the invention are compounds containing at least two isocyanate-reactive hydrogen atoms and having molecular weights in the range from 32 to 400. In this case, too, the compounds in question are compounds containing hydroxyl groups and/or thiol groups and/or carboxyl groups, preferably compounds containing hydroxyl groups and/or amino groups which are used as chain extenders or cross-linking agents. These compounds generally contain from 2 to 8 isocyanate-reactive hydrogen atoms, preferably 2 or 3 reactive hydrogen atoms.

Examples of compounds such as these are ethylene glycol, 1,2-propylene glycol and 1,3-propylene glycol, 1,4-butylene glycol and 2,3-butylene glycol, 1,5-pentane diol, 1,6-hexane diol, 1,8-octane diol, neopentyl glycol, 1,4-bis-hydroxymethyl cyclohexane, 2-methyl-1,3-propane diol, glycerol, trimethylol propane, 1,2,6-hexane triol, trimethylol ethane, pentaerythritol, quinitol, mannitol and sorbitol, diethylene glycol, triethylene glycol, tetraethylene glycol, polyethylene glycols with a molecular weight of up to 400, dipropylene glycol, polypropylene glycols with a molecular weight of up to 400, dibutylene glycol, polybutylene glycols with a molecular weight of up to 400, 4,4'-dihydroxy diphenyl propane, dihydroxy methyl hydroquinone, ethanolamine, diethanolamine, triethanolamine, 3-aminopropanol, ethylene diamine, 1,3-diaminopropane, 1-mercapto-3-aminopropane, 4-hydroxy- or -aminophthalic acid, succinic acid, adipic acid, hydrazine, N, N'-dimethyl hydrazine, 4,4'-diaminodiphenyl methane, tolylene diamine methylene-bischloraniline, methylene-bis-anthranilic acid ester, diaminobenzoic acid esters and the isomeric chlorophenylene diamines. In this case, too, it is possible to use mixtures of different compounds containing at least two isocyanate-reactive hydrogen atoms and having a molecular weight in the range from 32 to 400.

It is also possible in accordance with the invention to use polyhydroxyl compounds containing high molecular weight polyadducts or polycondensates in finely dispersed or dissolved form. Modified polyhydroxyl compounds such as these are obtained by carrying out polyaddition reactions (for example reactions between polyisocyanates and aminofunctional compounds) or polycondensation reaction (for example between formaldehyde and phenols and/or amines) directly in situ in the abovementioned compounds containing hydroxyl groups. Processes such as these are described, for example, in German Auslegeschriften Nos. 1,168,075 and 1,260,142 and in German Offenlegungsschriften Nos. 2,324,134; 2,423,984; 2,512,385; 2,513,815; 2,550,796 2,550,797, 2,550,833 and 2,550,862. It is also possible, in accordance with U.S. Pat. No. 3,869,413 or German Offenlegungsschrift No. 2,550,860, to mix an aqueous polymer dispersion with a polyhydroxyl compound and subsequently to remove the water from the mixture. In cases where such polyhydroxyl compounds are used as starting component in the polyisocyanate polyaddition process, polyurethane plastics with considerably improved mechanical properties are formed in many cases.

The exclusive reaction of the mixtures according to the invention in the absence of other isocyanate-reactive components, with strongly elasticizing polyisocyanates such as, for example polyisocyantes of biuret structure as described in German Auslegeschrift No. 1,543,178 yields rigid, light-stable, scratch-resistant and solvent-resistant coatings and lacquers.

By propoxylating and/or oxyethylating the polyols, it is also possible to obtain polyether alcohols of high functionality which, in the case of high hydroxyl numbers, may be used for the production of rigid or semirigid cellular polyurethane plastics and, in the case of low hydroxyl numbers, as starting materials for highly elastic polyurethane foams (cf. German Offenlegungsschrift No. 2,639,083).

By reacting the mixtures produced in accordance with the invention of polyhydric alcohols with polybasic carboxylic acids of the above-mentioned type, for example phthalic acid, isophthalic acid, terephthalic acid, tetra- and hexahydrophthalic acid, adipic acid or maleic acid by the methods normally used for condensing polyesters, of the type described for example in Houben-Weyl, Methoden der organischen Chemie, Vol. XIV 12, page 40, it is possible to synthesize heavily cross-linked polyesters which, as additives to alkyd resins, improve their hardness. The hydroxyl-group-containing polyesters synthesized from the hydroxyl compounds produced in accordance with the invention may of course also be used as starting components for the production of polyurethane plastics.

For many purposes, it is preferred not to hydrogenate the mixtures according to the invention before they are used as starters in the production of polyether polyols, as described in the above-mentioned German Offenlegungsschrift No. 2,639,083. Instead it is best to directly ethoxylate and/or propoxylate the mixtures optionally only partially, in unreduced form in the presence of acid catalysts, preferably Lewis acids, such as boron trifluoride etherate, the complex of boron trifluoride and acetic acid or acetanhydride, antimony trichloride, aluminum chloride, etc.

In this way, significant acetalation or ketalation takes place simultaneously *in a single operation* by ring-opening addition of the oxirane with the carbonyl functions of the formose-sugar mixtures or the methylolated carbonyl compounds in accordance with the following scheme:

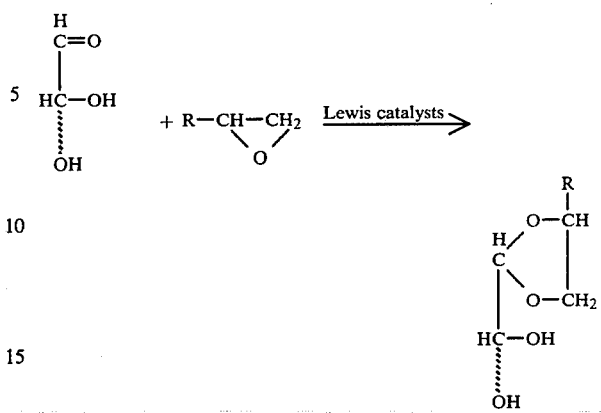

in which R represents for example, $CH_3$ or H.

Keto groups in the formoses are ketalized in accordance with the same scheme. However, the reaction may also be displaced in such a way that the oxiranes are polyadded in high yields with the hydroxyl groups of the formoses to form polyether polyols.

The Lewis-acid-catalyzed polyaddition of the propylene oxide with formose would appear to take place fairly selectively in accordance with the following scheme:

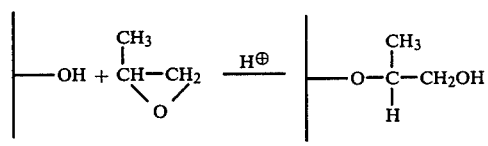

i.e. the reaction leads to the formation of primary hydroxyl groups, whereas the base-catalyzed polyaddition reaction takes place statistically, with the result that at least 50% of secondary hydroxyl groups are present in the polyether.

By reacting the mixtures obtained in accordance with the invention with acid anhydrides or mixed acid anhydrides, acrylonitrile, glycol carbonate, epichlorhydrin or dimethyl sulphate, it is also possible to obtain commercially useful intermediate products. In this connection, reference is made in particular to the cyanoethylation of the formoses with 1 to 50% by weight, based on formose, of acrylonitrile. This reaction is preferably carried out in the presence of basic catalysts of pH-values of from 7.5 to 9 at temperatures in the range from 40° to 100° C. and, with particular preference, at temperatures in the range from 60° to 90° C. Hydrogenation of the cyanoethylation products results in the formation of amino sugars which are of considerable interest for the production of polyurethane ureas and as hardeners for polyepoxides.

As already mentioned, the mixtures according to the invention form storable mixtures with waterglass (sodium or potassium silicate). For this purpose, the mixture according to the invention is generally used in a quantity of 100 parts by weight to about 10 to 100 parts by weight of waterglass. Mixtures such as these are very suitable for use as binders, although they may also be used as starting components for the production of inorganic-organic foams by reaction with polyisocyanates or prepolymers containing isocyanate groups by the processes described in German Offenlegungsschriften Nos. 1,770,384; 2,359,606; 2,359,607; 2,359,608; 2,359,609; 2,359,610 and 2,359,611.

In addition, the mixtures according to the invention have been found to be suitable mixing components for the relatively high molecular weight polyhydroxyl compounds described above and, in this connection, surprisingly improve the compatibility of various of these polyols with one another and with the other components of polyurethane recipes.

The present invention is illustrated by the following Examples in which the quantities quoted represent parts by weight and percent by weight, unless otherwise stated.

EXAMPLES

Example 1

Formose synthesis with cyclohexanone as co-catalyst 1000 g (12.33 moles) of a 37% standard commercial-grade aqueous formalin solution stabilized with methanol are mixed with 33 g of cyclohexanone and 5 g of lead acetate [$Pb(CH_3OO)_2.3H_2O$]. The resulting mixture is heated to 95° C. The pH-value of the reaction mixture is adjusted to between 6.5 and 7 by the continuous addition of 10% aqueous sodium hydroxide. After the addition of 210 ml of sodium hydroxide, the formaldehyde content of the mixture has fallen to 1.25%. The initially cloudy solution has become completely clear by the end of the reaction. The reaction mixture is cooled and desalted over ion exchangers. Concentration in a rotary evaporator gives 382 g of a pale yellow reaction product which contains 6.4% of water and has a sugar content of 55.2%, expressed as glucose.

After the formose has been hydrogenated and the formitol thus obtained silylated, analysis by gas chromatography reveals the following component distribution:

|   | $C_2$ | $C_3$ | $C_4$ | $C_5$ | $C_6$ | $C_7$ | $C_8$ |
|---|---|---|---|---|---|---|---|
| % | 0.27 | 2.74 | 4.73 | 16.73 | 43.29 | 20.84 | 4.23 |

The formitol contains 7.07% of tetramethylol cyclohexanol.

Example 2

1000 g of the 37% formalin solution of Example 1 are mixed with 66 g of cyclohexanone and 5 g of $Pb(CH_3COO)_2.3H_2O$. The resulting mixture is heated to 95° C. The pH-value of the reaction mixture is adjusted to between 5 and 5.5 by the continuous addition of 10% sodium hydroxide. After the addition of 315 ml of sodium hydroxide, the formaldehyde content of the mixture has fallen to 1.14%. The initially cloudy solution is completely clear and desalted over ion exchangers. Concentration in a rotary evaporator gives 369 g of a colorless reaction product which contains 5.2% of water and which has a sugar content of 54.1%, expressed as glucose.

After the formose has been hydrogenated and the formitol thus obtained silylated, gas-chromatographic analysis reveals the following component distribution:

|   | $C_2$ | $C_3$ | $C_4$ | $C_5$ | $C_6$ | $C_7$ | $C_8$ |
|---|---|---|---|---|---|---|---|
| % | 0.25 | 2.5 | 3.6 | 18.82 | 36.94 | 18.80 | 6.05 |

The formitol contains 13.03% of tetramethylol cyclohexanol.

Example 3

1500 g of the 37% formalin solution of Example 1 (18.5 moles formaldehyde) and 491 g of cyclohexanone (5 moles) are heated with stirring to 95° C., followed by the addition of 56 g of a 50% aqueous solution of the formose used as co-catalyst in Example 1 of German Offenlegungsschrift No. 2,639,084 and 15 g of lead acetate trihydrate. The pH-value of the mixture is adjusted to 7.5 by the addition of 10% sodium hydroxide. After the reaction has started (increase in the temperature of the mixture to 100°-102° C.), the pH is kept between 6.5 and 7.0 by the addition of more sodium hydroxide. After about 20 minutes, the reaction is stopped at a residual formaldehyde content of 1.5% by cooling with ice water. Total consumption of 10% sodium hydroxide: 123 g. Most of the lead is precipitated with 10 g of sodium bicarbonate and the solution is fully desalted over ion exchangers after the deposit has been filtered off under suction. 800 g of a modified formose having a water content of 5.8% and a sugar content (expressed as glucose) of 37% are obtained.

The viscosity of the modified formose at 20° C. amounts to 5000 mPa.s for a water content of 10%. A formose produced in the same way, but without the addition of cyclohexanone, only has a comparable viscosity of 5300 mPa.s at 50° C.

Example 4

The procedure is as in Example 3, except that, instead of lead acetate, 18.5 g of powdered calcium hydroxide (0.25 moles) are used as catalyst, being added in portions to the reaction mixture. An initial pH-value of from 7.0 to 7.5 is adjusted in this way. The reaction mixture is then kept at a pH-value of from 7.0 to 8.0 by the addition of 10% sodium hydroxide (total consumption 395 g). After about 30 minutes, the reaction is stopped at a residual formaldehyde content of 0.4% by cooling with ice water and the calcium precipitated in sulphate form with 0.25 mole of dilute sulphuric acid. After it has been filtered off from the deposit under suction, the solution is fully desalted over ion exchangers and concentrated. 850 g of a modified formose having a water content of 5.1% and a sugar content of 16.6% are obtained. The viscosity of the formose containing 10% of water is 13,300 mPa.s at 20° C.

The viscosity of a formose produced in the same way, but without the addition of cyclohexanone, is more than 100,000 mPa.s at 20° C. for a water content of 10%.

Example 5

1500 g of the 37% formalin solution of Example 1 (18.5 moles of formaldehyde) are heated to reflux temperature (approximately 75° C.) together with 288 g of n-butyraldehyde (4 moles). After 56 g of the same co-catalyst solution as in Example 3 and 15 g of lead acetate trihydrate have been added, the pH-value of the solution is adjusted to 8.0 with 10% sodium hydroxide. After the reaction has started, the pH-value is kept between 6.5 and 7.5 by the addition of more sodium hydroxide. A total of 296 g of 10% sodium hydroxide are consumed. After a reaction time of 70 minutes, the reaction is stopped at a residual formaldehyde content of 1.2% by cooling with ice water. After neutralization with 7% nitric acid, the product is fully desalted over ion exchangers and concentrated in a thin layer evaporator to 760 g of a thinly liquid syrup containing 37.5% of sugar and 10% of water and having a viscosity of 9600 mPa.s at 20° C.

Example 6

1500 g of the 37% formalin solution of Example 1 (18.5 moles of formaldehyde) are heated with stirring to 95° C., followed by the addition of 56 g of the co-catalyst solution used in Example 3 and 15 g of lead acetate trihydrate. The pH-value of the solution is adjusted to 7.5 with 10% NaOH, after which the reaction begins. The pH-value of the reaction mixture is kept between 6.5 and 7.0 by the repeated addition of sodium hydroxide to a total consumption of 10% sodium hydroxide of 188 g. After approximately 10 minutes, the mixture still contains 15.1% of formaldehyde. 230 g of n-butyraldehyde (3.2 moles) are then added over a period of 10 minutes. The pH-value of the solution falls to 5.4, the internal temperature to 75° C. and the formaldehyde content to 9.8%. The reaction is continued with addition of sodium hydroxide in the pH-range from 6.5 to 7.5 and at an internal temperature of 75° to 85° C. After a total of 65 minutes, the reaction is stopped at a residual formaldehyde content of 1.5% by cooling with ice water.

Complete desalting by means of ion exchangers and concentration in a rotary evaporator gives a formose containing 10% of water and 57% of sugar, expressed as glucose, and having a viscosity of 80,200 mPa.s at 20° C.

Example 7

The reaction mixture of Example 7 is adjusted to pH 6.5 by the addition of 10% sodium hydroxide at 100° C., as a result of which the condensation reaction begins. After 10 minutes, the formaldehyde content of the solution has fallen to 15.6%. 288 g of isobutyraldehyde (4 moles) are then added over a period of 10 minutes. The mixture is kept at 65° to 74° C. and at a pH-value of from 6.8 to 7.2 (total consumption of 10% sodium hydroxide of 196 g) until the reaction is over. After 165 minutes, the reaction is stopped at a residual formaldehyde content of 1.7% by cooling with ice water.

After complete desalting by means of ion exchangers, removal of most of the water present leaves a modified formose containing 10% of water and 41.3% of sugar, expressed as glucose, and having a viscosity of 24,300 mPa.s at 20° C.

Example 8

The reaction mixture of Example 7 is adjusted to pH 6.8 by the addition of 10% sodium hydroxide at 100° C., as a result of which the condensation reaction begins. After 15 minutes, the formaldehyde content of the solution has fallen to 17.2%. 393 g of cyclohexanone (4 moles) are added over a period of 5 minutes, the pH-value of the reaction mixture falling to 5.7. The pH-value is then kept between 6.0 and 6.2 (total consumption of 10% sodium hydroxide of 112 g). After 37 minutes, the reaction is stopped at a residual formaldehyde content of 1.8% by cooling with ice water.

After complete desalting by means of ion exchangers, removal of most of the water leaves a modified formose containing 10% of water and 55.4% of sugar, expressed as glucose, and having a viscosity of 53,200 mPa.s at 20° C.

Example 9

This example shows that the mixtures according to the invention may also be produced by mixing aqueous or alcoholic formoses produced by any method or α-aldolated formoses with aqueous formaldehyde and subsequently using the free formaldehyde by the addition of aldehydes or ketones for α-methylolation of the aldehydes and ketones. As shown by parallel tests, up to about 30% by weight of non-α-alkolated formose is also methylolated in the α-position to the carbonyl groups in a secondary reaction.

(a) 100 g of a preformed, fully desalted 50% formalin solution produced by the process described in German Offenlegungsschrift No. 2,639,084 are mixed with 200 g of a 30% formaldehyde solution (2 moles) and 72 g of n-butyraldehyde (1 mole) to form a dispersion. Following the addition of 4 g of dimethyl benzylamine, the mixture is heated with intensive stirring to 70° C. The temperature of the mixture is increased to 95°% over a period of another 4 hours by the continuous addition of another 11 parts by weight of dimethyl benzylamine at pH 8.5.

After complete desalting by means of ion exchangers and concentration of the mixture by distillation to a water content of around 5.6% in a rotary evaporator at 55° C./16 Torr, a modified formose having a viscosity of 109,112 mPa.s at 25° C. is obtained. In contrast, the fully desalted starting formose used, for a water content of 5.6%, has a viscosity which cannot be measured at 25° C. but which, on the basis of extrapolation curves, amounts to more than 550,000 mPa.s at 25° C.

(b) The α-aldolated formose used is produced as follows:

500 g of a fully desalted aqueous solution containing 50% by weight of formose produced in accordance with Example 1 of German Offenlegungsschrift No. 2,639,084 (250 g of formose solids; average molecular weight approximately 166; approximately 1.5 moles) are mixed with 150 g of a 30% formalin solution (approximately 1.5 moles) and 10 g of triethylamine. After heating while stirring to 85° C., the reduction in the formaldehyde content is followed by titration with sodium sulphite. After only 45 minutes, the formaldehyde content of the solution has fallen from 6.3% to 0.5% and the α-aldolation reaction has ended. The hot solution is clarified by the addition of 8 g of active carbon and then filtered, leaving an only slightly yellowish colored solution predominantly containing α-aldolated formoses having the following idealized compositions:

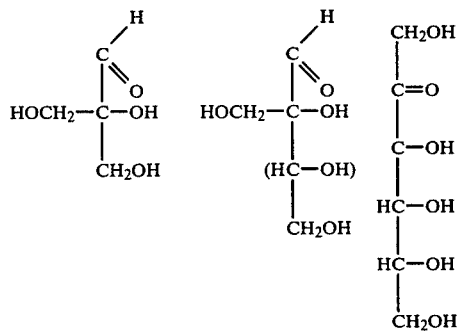

-continued n = 1-7

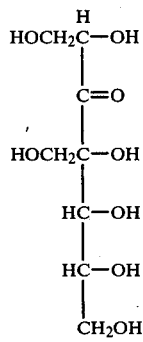

The controlled α-aldolation reaction gives formoses which contain an average of at least 2 primary hydroxyl groups per molecule and which have a greater reactivity than the starting formoses with respect to polyisocyanates.

In this procedure, the α-aldolation is, surprisingly, highly favored over possible crossed Cannizzaro reactions. As may be concluded from the analytically determined formation of triethyl ammonium formate, only about 3 g of the formaldehyde used (approximately 7% of the total quantity) enters into crossed Cannizzaro reactions.

The viscosity of the aldolated formose thus produced, which is concentrated to a water content of 5.2% in a rotary evaporator, cannot be measured either at 25° C. or at 35° C. On the basis of extrapolation curves, the viscosity is more than 570,000 mPa.s. At 50° C., the viscosity of this aldolated formose is measurable and is 25,736 mPa.s. The average molecular weight of this α-aldolated formose is around 198.

Production of the mixtures according to the invention: The procedure is exactly the same as in section (a) of this example using 50 g of the formose solution described above diluted to a water content of 50%. A modified formose is obtained which, for a water content of approximately 5.2%, has a viscosity of 104,000 mPa.s at 25° C.

The mixtures (a) and (b) according to the invention may also be produced by mixing the quantities by weight of formose or α-aldolated formose mentioned in (a) and (b) with 1 mole of preformed methylolated n-butyraldehyde having the following composition:

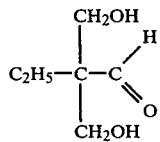

Example 10

Manufacture of a polyurethane foam using the modified formose of example 3.

21.6 parts of a mixture of 3 parts of the modified formose of example 3, 0.5 parts of glycerol and 0.5 parts of the adduct of 1 mol of water and 1 mol of ε-caprolactam,
20.4 parts of the propoxylation product of ethylene diamine having an OH number of 450,
7.0 parts of tri-β-chloroethylphosphate,
18.7 parts of monofluortrichloromethane,
0.15 parts of dimethylbenzylamine,
0.75 parts of a commercial silicone stabiliser (L-5420 of UCC) and
81 parts of a polyisocyanate mixture obtained by phosgenation of an aniline/formaldehyde-condensate having an NCO content of 29%
are mixed. The mixture is allowed to foam in an open mould at room temperature. A semi-rigid polyurethane foam having very fine cells is obtained.

What is claimed is:

1. Isocyanate reactive mixtures comprising
    (a) from 20 to 90% by weight, based on (a)+(b), of a mixture of polyhydric alcohols, hydroxy aldehydes and hydroxy ketones which have been obtained by the condensation of formaldehyde hydrate
    (b) from 10 to 80% by weight, based on (a)+(b), of aldehydes and/or ketones methylolated in the α-position and incapable of enediol formation
    (c) from 0 to 50% by weight, based on (a)+(b), of water, and
    (d) from 0 to 100% by weight, based on (a)+(b), of monosaccharides and/or disaccharides.

2. The mixtures of claim 1 wherein component (a) comprises from 40 to 70% by weight, component (b) comprises from 25 to 60% by weight, and component (c) comprises from 0.3 to 30% by weight, all weights based on (a)+(b).

3. The mixtures of claim 2, wherein component (c) comprises from 0.8 to 10% by weight based on (a)+(b).

4. The mixtures of claim 2, wherein component (d) comprises from 10 to 50% by weight, based on (a)+(b).

5. The mixtures of claim 1 wherein component (a) comprises formoses having an average molecular weight of from 92 to 360 and a sugar content, expressed as glucose having a molecular weight of 180, of from 4 to 85% by weight.

6. The mixtures of claim 5, wherein said formoses have an average molecular weight of from 100 to 240 and a sugar content of from 6 to 72% by weight.

7. The mixtures of claim 1, wherein component (b) comprises aliphatic, cycloaliphatic, or araliphatic aldehydes and ketones containing from 2 to 15 carbon atoms.

8. The mixtures of claim 7, wherein said aldehydes and ketones contain from 2 to 9 carbon atoms.

9. The mixtures of claim 1, wherein component (b) is selected from the group consisting of

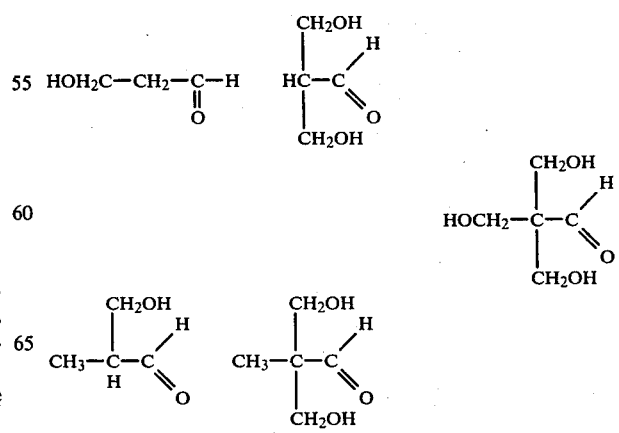

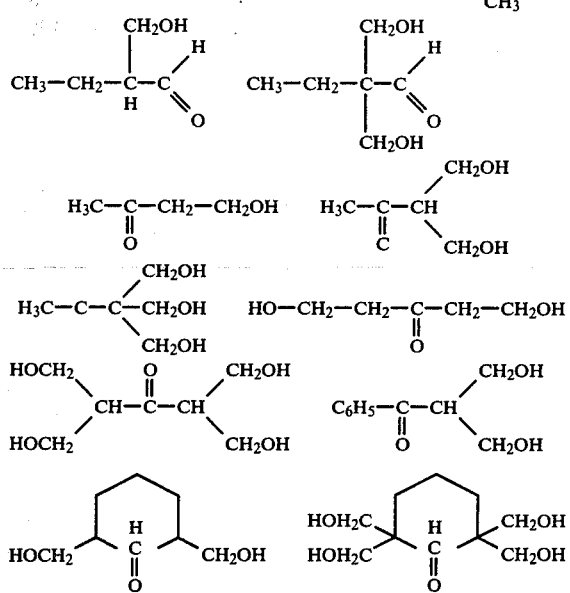

10. The mixtures of claim 1, wherein the aldehydes and/or ketones of component (b) are selected from the group consisting of n-butyraldehyde, isobutyraldehyde, acetone and cyclohexanone.

11. A process for producing isocyanate-reactive mixtures comprising condensing aqueous formalin solutions and/or paraformaldehyde dispersions containing from 20 to 65% by weight of formaldehyde at pH-values of from 4 to 9 and at a reaction temperature of from 70° to 110° C. in the presence of (a) soluble or insoluble salts of metals of the Second to Fourth Main Group or of the First to Eighth Secondary Group of the Periodic System of Elements or metal ions of said groups and/or subgroups fixed to a high molecular weight support, (b) aldehydes and/or ketones capable of α-aldolation or their α-methylolation products and, optionally (c) co-catalysts based on compounds capable of enediol formation, until the residual formaldehyde content is from 0 to 10% by weight, based on the reaction mixture; subsequently removing the catalyst; and concentrating the reaction product to the desired water content.

12. The process of claim 11, wherein said pH-value is from 5 to 8, and wherein the condensation is continued until the residual formaldehyde content is from 0.5 to 6% by weight.

13. A process for producing isocyanate-reactive mixtures comprising condensing aqueous formalin solutions and/or paraformaldehyde dispersions containing from 20 to 65% by weight of formaldehyde at pH-values of from 4 to 9 at a reaction temperature of from 70° to 110° C. in the presence of (a) soluble or insoluble salts of metals of the Second to Fourth Main Group or the First to Eighth Secondary Group of the Periodic System of Elements or metal ions of said groups and/or subgroups fixed to a high molecular weight support, and (b) co-catalysts based on compounds capable of enediol formation, up to a conversion of from 40 to 95% by weight, based on the formaldehyde used, to form mixtures of low molecular weight polyhydric alcohols, hydroxy aldehydes and hydroxy ketones; binding the residual formaldehyde by the addition of α-aldolatable carbonyl compounds incapable of enediol formation; freeing the reaction product from the catalyst; and concentrating reaction product to the desired water content.

14. The process of claim 13 wherein the condensation in continued up to a conversion of from 70 to 90% and wherein the pH-value is from 7 to 9.

15. The process of claim 13 wherein said pH-value is from 5 to 8, and wherein said conversion is from 70 to 90%.

16. A process for producing isocyanate-reactive mixtures comprising mixing (a) an aqueous or alcoholic solution of a mixture of low molecular weight polyhydric alcohols, hydroxy aldehydes and hydroxy ketones, which have been obtained by the autocondensation of formaldehyde hydrate with (b) α-aldolatable carbonyl compounds; and subsequently methylolating the mixture by the addition of aqueous formaldehyde.

17. The process of claim 16 wherein from 20 to 300% of the quantity of formaldehyde required to obtain complete methylolation of the α-aldolatable carbonyl compound is added.

18. The process of claim 17, wherein from 50 to 150% of the quantity of formaldehyde required to obtain complete methylolation of the α-aldolatable carbonyl compound is added.

19. The process of claim 17 wherein the methylolation reaction is conducted to a pH of from 7 to 9 and a temperature of from 10° to 65° C.

20. The process of claim 19, wherein the pH-value is from 7.5 to 8 and the temperature is from 20° to 50° C.

21. The process of claim 16 wherein following the methylolation reaction excess water is removed.

22. The process of claim 21 wherein the excess water is removed in a thin-film evaporator under a vacuum of from 1 to 18 Torr and at a temperature of from 35° to 60° C.

23. A process for the production of optionally cellular polyurethane plastics comprising reacting (a) polyisocyanates with (b) polyhydroxyl compounds having a molecular weight of less than 400, optionally (c) polyhydroxyl compounds having a molecular weight of from 400 to 10,000 and, optionally, other isocyanate-reactive compounds, optionally in the presence of (d) blowing agents, catalysts, and fillers wherein component (b) comprises an isocyanate-reactive mixture comprising (a) from 20 to 90% by weight, based on (a)+(b), of a mixture of polyhydric alcohols, hydroxy aldehydes and hydroxy ketones which have been obtained by the condensation of formaldehyde hydrate, (b) from 10 to 80% by weight, based on (a)+(b), of aldehyde and/or ketones methylolated in the α-position and incapable of enediol formation (c) from 0 to 50% by weight, based on (a)+(b), of water, and (d) from 0 to 100% by weight, based on (a)+(b), of monosaccharides and/or disaccharides.

24. The process of claim 23, wherein component (c) comprises from 4 to 25% by weight.

25. The process of claim 24, wherein component (c) comprises from 8 to 20% by weight.

26. The process of claim 23, wherein the isocyanate index is from 20 to 70.

27. The process of claim 26, wherein the isocyanate index is from 30 to 60.

28. The process of claim 27, wherein the isocyanate index is from 35 to 55.

29. The process of claim 23 wherein component (c) comprises from 0 to 4% by weight.

30. The process of claim 29, wherein component (c) comprises from 0.7 to 3% by weight.

31. The process of claim 23, wherein component (b) comprises from 5 to 30% by weight based on the total of (b)+(c).

* * * * *